United States Patent [19]

Tanikella

[11] 4,404,411

[45] Sep. 13, 1983

[54] HYDROGENOLYSIS OF POLYOLS TO ETHYLENE GLYCOL IN NONAQUEOUS SOLVENTS

[75] Inventor: Murty S. S. R. Tanikella, Wilmington, Del.

[73] Assignee: E. I. Du Pont de Nemours and Company, Wilmington, Del.

[21] Appl. No.: 344,302

[22] Filed: Feb. 1, 1982

[51] Int. Cl.$^3$ .............................................. C07C 21/20
[52] U.S. Cl. ...................................................... 568/861
[58] Field of Search ........................................ 568/861

[56] References Cited

U.S. PATENT DOCUMENTS

| | | | |
|---|---|---|---|
| 1,963,997 | 6/1934 | Larchar | 260/156.5 |
| 2,004,135 | 6/1935 | Rothrock | 260/156.5 |
| 2,325,207 | 7/1943 | Stengel et al. | 260/635 |
| 2,394,588 | 2/1946 | Bean | 568/851 |
| 2,451,945 | 10/1948 | Hanford | 568/851 |
| 2,852,570 | 9/1958 | Conradin et al. | 260/635 |
| 2,965,679 | 12/1960 | Conradin et al. | 260/635 |
| 3,030,429 | 4/1962 | Conradin et al. | 260/635 |
| 3,105,099 | 9/1963 | Duerden | 568/851 |
| 3,396,199 | 8/1968 | Kasehagen | 260/635 |

FOREIGN PATENT DOCUMENTS 422718   4/1974   U.S.S.R. .

OTHER PUBLICATIONS

Van Ling et al., *J. App. Chem.* 19, 43–45, (1969).
Vasyunina et al., *Khimicheskaya Promishlennost,* 1962, (2), 82–86.
Clark, I. T., *Industrial Engineering Chemistry,* vol. 50, pp. 1125–1126, (1958).
Balandin et al., Uzbekskii khimicheskii zhurnal 6, 64–72, (1962).
Vasyunina et al., *Kinetika i Kataliz,* 4, 443–449, (1963).
Vasyunina et al., *Kinetika i Kataliz,* 4, 156–162, (1963).
Vasyunina et al., *Proc. Academy of Sciences USSR,* Chemistry Section 169, Nos. 4–6, 767–769, (1966).
Poletaeva et al., *Bull. Academy of Science USSR,* Division of Chemical Science, Jun. 10, 1977, 2412–2414.

*Primary Examiner*—J. E. Evans

[57] ABSTRACT

Process for hydrogenolysis of polyols to ethylene glycol in nonaqueous solvents yields high conversion to ethylene glycol in presence of at least about 10 mol percent of a strong base at a temperature of 235° C. to 315° C.

16 Claims, No Drawings

HYDROGENOLYSIS OF POLYOLS TO ETHYLENE GLYCOL IN NONAQUEOUS SOLVENTS

TECHNICAL FIELD

This invention relates to a catalytic process for the hydrogenolysis of polyols to ethylene glycol.

BACKGROUND INFORMATION

Polyols, such as glycerol, erythritol, xylitol and sorbitol, undergo hydrogenolysis in the presence of a hydrogenation catalyst and an inorganic hydroxide base to yield, primarily, glycerol, ethanediol and 1,2-propanediol. Other products may include tetritols, lactic acid, methanol, ethanol and propanol. Xylitol and sorbitol are available from biomass, such as forest and agricultural products, from which cellulose and hemicellulose can be extracted, hydrolyzed and reduced to these polyols.

Until recently, it was considered that the most economically rewarding product of the hydrogenolysis of polyols was glycerol, and that ethanediol, hereinafter referred to as ethylene glycol, could be produced more economically from other hydrocarbon sources, in particular, petroleum sources. Now, due to the scarcity and expense of petroleum, an alternate route to ethylene glycol utilizing renewable and less costly resources is desirable.

The following references provide further background information.

U.S. Pat. No. 2,965,679 discloses hydrogenolysis of polyols at 200° to 300° C., 500 to 1,000 atm (50 to 101 MPa) and pH 8 to 10. The pH may be attained by the addition of calcium hydroxide.

U.S. Pat. No. 3,030,429 discloses hydrogenolysis of sorbitol and mannitol at 180° to 250° C., up to 1,000 atm (101 MPa) and pH 11 to 12.5. The pH may be attained by the addition of calcium hydroxide.

U.S. Pat. No. 2,852,570 discloses a process for the hydrogenolysis of hexites, e.g., sorbitol, to glycerol and ethylene glycol in the presence of a catalyst which contains only cobalt and nickel in addition to a carrier, e.g., alkaline earth oxides, at 200° to 220° C. and 100 to 200 atm (10 to 20 MPa). The catalyst, added in amounts of, e.g., 50 weight percent based on sorbitol, comprises, e.g., 75 percent magnesium oxide.

U.S. Pat. No. 2,325,207 discloses hydrogenolysis of carbohydrates and polyols in the presence of 5 to 7 weight percent of a catalyst comprised of a copper hydroxide and an iron and/or magnesium hydroxide, at 150° to 250° C. in an alkaline environment which can be achieved by the addition of an excess of alkali, e.g., sodium hydroxide in the amount required to neutralize initial acidity and to coprecipitate the hydroxides, plus 2 to 15 weight percent, based on substrate.

U.S. Pat. No. 2,004,135 discloses hydrogenolysis of polyols in the presence of an amount of a weakly alkaline buffer sufficient to maintain a weakly alkaline reaction mixture, preferably calcium carbonate although aluminum hydroxide is noted as useful, at 200° to 300° C., preferably 250° C., and 1000 to 4500 psi (7 to 31 MPa).

U.S. Pat. No. 1,963,997 discloses hydrogenolysis of polyols at 100° to 300° C. and, e.g., 3000 psi (21 MPa) using a catalyst "containing a hydrogenating and a dehydrating component", e.g., nickel-chromium oxide.

U.S. Pat. No. 3,396,199 discloses hydrogenolysis of sugars in the presence of an alkaline earth metal oxide, hydroxide or weak acid salt in proportion to furnish from 0.25 to 1.0 weight percent of calcium oxide equivalent, based on the weight of substrate, at 190° to 230° C. and at least 500 psi (3.5 MPa).

U.S.S.R. Pat. No. 422,718 discloses hydrogenolysis of sugars at 235° C. and 100 to 150 atm (10 to 15 MPa), with stirring, in the presence of, e.g., 2.5 weight percent of calcium hydroxide, 2.5 weight percent of ferric chloride hexahydrate and 8 percent nickel on kieselghur, based on substrate.

Balandin, A. A., et al., *Uzbekskii khimicheskii zhurnal*, Vol. 6, pp. 64–72 (1962), discloses a process for the hydrogenolysis of xylitol in the presence of 1 weight percent of calcium oxide, based on xylitol, at 200° to 230° C. and 200 atm (20 MPa).

Vasyunina, N. A., et al., *Kinetika i Kataliz*, 4, 156–162 and 433–449 (1963) disclose experiments designed to determine the effects of calcium oxide, barium oxide and sodium hydroxide, and the effects of temperature (200° to 245° C.) and pressure (100 to 250 atm) (10 to 25 MPa), on hydrogenolysis of xylitol.

Clark, I. T., *Industrial Engineering Chemistry*, Vol. 50, pp. 1125–1126 (1958), discloses hydrogenolysis of sorbitol in the presence of up to 3 weight percent of calcium hydroxide, based on sorbitol, at 215° to 245° C. and up to 5600 psi (39 MPa).

van Ling, G. and Vlugter, J. C., *Journal of Applied Chemistry*, Vol. 19, pp. 43–45 (1969), discloses hydrogenolysis of saccharides and hexitols in the presence of up to 5 weight percent of calcium hydroxide, based on substrate, at 200° to 250° C. and 100 and 300 atm (10 to 30 MPa).

Vasyunina, N. A., et al., *Proc. Academy of Sciences USSR*, Chemistry Section, Vol. 169, Nos. 4–6, 767–769 (1966), discloses hydrogenolysis of monosaccharides and polyols in the presence of various inorganic hydroxide bases, carbonates of calcium, barium and sodium, acetates of calcium and barium and certain nitrogen-containing bases at pH 7.5 to 8.5, at 230° C. and 200 atm (20 MPa).

Poletaeva, T. I., et al., *Bull. Academy of Science USSR*, Division of Chemical Science, June 10, 1977, 2412–2414, discloses hydrogenolysis of glucose using Ni-Al$_2$O$_3$ catalysts at 215° to 240° C. and 120 atm (12 MPa) in the presence of 3 to 3.7 percent of calcium hydroxide based on the weight of glucose.

Heretofore, studies into the hydrogenolysis of polyols have been directed predominantly to reactions carried out in aqueous solutions. This fact is illustrated by the observation that of the above references, only three suggest the use of nonaqueous solvents. These are U.S. Pat. Nos. 2,004,135, 1,963,997 and 3,396,199.

It is an object of this invention to provide a catalytic process for the hydrogenolysis of polyols in nonaqueous solvents, which process results in high conversion of the polyols to useful products, particularly ethylene glycol. It is also an object to provide such a process in which the solvent is a $C_{1-4}$ monohydric alcohol, particularly methanol and ethanol.

The above objects are achieved by the use of large amounts of a base and by use of high temperature in nonaqueous solvents.

DISCLOSURE OF THE INVENTION

For further comprehension of the invention and of the objects and advantages thereof, reference may be made to the following description and to the appended claims in which the various novel features of the invention are particularly set forth.

The invention resides in the process for hydrogenolysis of polyols to ethylene glycol in which process the polyols are contacted and reacted with hydrogen in a nonaqueous solvent in the presence of a hydrogenation catalyst and at least about 10 mol percent of a base at a temperature of at least about 225° C.

The invention also resides in said process wherein the solvent is a $C_{1-4}$ monohydric alcohol and in said process wherein, additionally, the base is an alkoxide corresponding to the solvent.

It has been found that use of the process disclosed and claimed herein results in high conversion of the polyols to useful products. In addition to ethylene glycol which is the most preferred product, other useful products are propylene glycol and glycerol and other products such as erythritol and monohydric alcohols.

Useful nonaqueous solvents include those in which the polyols are at least partly soluble under reaction conditions and which remain substantially unreacted and do not interfere with the hydrogenolysis reaction. Solvents which are useful include, e.g., methanol, ethanol, propanols, butanols, ethylene glycol, propylene glycol, lower polyols such as glycerol, tetrahydrofuran and cyclohexane. As an example of a solvent which is not useful, dimethyl formamide is mentioned.

The preferred solvents are $C_{1-4}$ monohydric alcohols and of these, methanol and ethanol, especially methanol, are particularly preferred. Use of protic solvents results in higher conversion to ethylene glycol than does use of, e.g., cyclohexane.

A large amount of a compound which is a base, preferably a strong base, in the selected solvent is employed as a promoter. When the solvent is a $C_{1-4}$ monohydric alcohol, the preferred strong base is the corresponding alkoxide of an alkali metal or of calcium, barium or strontium. Other strong bases, including compounds which convert to the corresponding alkoxides in situ, can also be used in alcohol solvents. Included among these are inorganic hydroxide and oxide bases such as hydroxides and oxides of alkali metals or of calcium, strontium or barium. When such bases are employed, the preferred solvent is methanol or ethanol, especially methanol, because use of such bases in these solvents results in conversion to ethylene glycol approximately the conversion achieved using the more preferred alkoxide bases.

Use of strong bases can result in at least about 25 weight percent conversion, based on all products, of xylitol to ethylene glycol in methanol, with total conversion being at least about 85 weight percent. Use of preferred bases can result, when preferred conditions of pressure and temperature are employed, in at least about 35 weight percent conversion of xylitol to ethylene glycol.

Metals which have been shown to be especially advantageous in alkoxides and hydroxides are sodium and calcium; sodium is preferred because its use has resulted in higher conversion to ethylene glycol.

Xylitol and sorbitol are preferred polyols because they are readily available from cellulose and hemicellulose which are derivable from biomass. Pentitols are preferred over hexitols because hydrogenolysis of xyltiol results in higher conversion to ethylene glycol than does hydrogenolysis of sorbitol. Preferably, due to economic considerations, the polyols are introduced into the reaction mixture in at least a 15 weight percent solution and, more preferably, due to convenience in handling, and economic considerations, i.e., higher throughput, in a 40 to 70 weight percent solution, although the concentration is not critical. They can be used separately or as a mixture of polyols. The presence in the reaction mixture, which is basic, of other substances which do not significantly adversely affect the reaction is not precluded. Further, the invention includes the described process wherein the polyols are introduced into the reaction mixture in the form of other compounds, such as ketones and saccharides, which are reduced to polyols in situ.

Hydrogen is preferably added to the reaction mixture in at least an amount stoichiometrically required to hydrogenolyze all of the polyols to ethylene glycol. Any hydrogenation catalyst may be used, e.g., nickel, palladium, and platinum. The catalyst may be free or supported. The amount of catalyst is preferably at least about 0.5 weight percent. The preferred catalyst, in most cases, is nickel on silica/alumina. Use of nickel on silica alumina, without a base, can result in up to about 15 weight percent of ethylene glycol.

In general, the bases are employed in amounts of at least about 10 mol percent based on the polyols, preferably at least about 15 mol percent, although the optimum base concentration varies depending upon the substrate, the base and the solvent and perhaps also on the conditions employed. For example, in methanol, use of at least about 20 mol percent of alkoxide, hydroxide or oxide base, based on polyol, is more preferred; in the hydrogenolysis of sorbitol in methanol, use of at least about 25 mol percent, especially at least about 40 mol percent, of such base, based on polyol, is more preferred. (See Tables 9 and 10, below.)

The reaction is carried out at a temperature of at least about 225° C., e.g., 235° to 325° C. The preferred temperature is about 240° C. to about 315° C. A wide range of pressures may be used. For example, in batch reactions, the hydrogen partial pressure, prior to heating, should be at least about 1000 psi (6.9 MPa), preferably about 2000 to 7000 psi (13.8 to 48.3 MPa).

The reaction may be carried out in a batch, continuous or semi-continuous manner. The catalyst may be fluidized or static as with a bed of catalyst over which the reaction mixture is caused to flow.

EXAMPLES

Following are examples which are illustrative of the invention. All reactions were carried out substantially by the following procedure.

The polyol was mixed in a solvent with nickel on silica/alumina and a strong base and stirred until the reaction mixture appeared to be homogeneous or uniform. The mixture was then charged to a 10 cm³ pressure bomb which was placed behind a protective barrier.

The pressure bomb was evacuated, pressurized with hydrogen at room temperature and then heated over a period of about 30–50 minutes to the reaction temperature.

After the reaction time, the pressure bomb was allowed to cool to room temperature. The reaction products, undiluted, were filtered through a thin layer of Celite ® analytical filter aid and analyzed by gas chromatography.

The conditions and results of the examples are tabulated below. Products reported are Alc (methanol and ethanol), EG (ethylene glycol), PG (propylene glycol), X (xylitol), T (tetritols) and G (glycerol); also reported is Unr (unreacted, i.e., one of glycerol, erythritol, xylitol or sorbitol) and Oth (other, e.g., higher polyols and degradation products). These are reported as weight percentages based on the total weight of all products recovered. The solvents are reported as MeOH (methanol), EtOH (ethanol), i-PrOH(isopropanol), t-BuOH(t-butanol), THF(tetrahydrofuran) and cyclohexane. The reported alkoxide bases are similarly abbreviated, e.g., sodium methoxide is reported as NaOMe. The polyol was present in an amount of 40 weight percent based on the total weight of the reaction mixture except where otherwise indicated. Each reported weight percent of the catalyst is based on the weight of the nickel or palladium relative to the total weight of the reaction mixture. The amounts of base are reported as mol percent, i.e., moles of cation relative to moles of polyol. Each reported reaction time is the length of time for which the reaction mixture was held at the specified reaction temperature. Each reported pressure is the hydrogen partial pressure prior to heating.

In several similar reactions in water, greater than about 90 percent of all materials, including products and starting materials, were recovered. It is believed that in the following examples, product recovery was about the same. Some examples appear in more than one table.

TABLE 1

Weight percent of products from hydrogenolysis of xylitol in methanol or ethanol at 275° C. and 4000 psi (27.6 MPa), for one hour using 0.8 weight percent of nickel on silica/alumina and 20.5 mol percent of the indicated corresponding alkoxide base or, no base.

|     | MeOH NaOMe | MeOH — | EtOH NaOEt |
|-----|------------|--------|------------|
| EG  | 45         | 15     | 41         |
| PG  | 33         | 8      | 41         |
| G   | 5          | 11     | 2          |
| T   | 2          | 1      | 0          |
| Alc | 1          | 1      | 2          |
| Oth | 14         | 8      | 14         |
| Unr | 0          | 56     | 0          |

TABLE 2

Weight percent of products from hydrogenolysis of sorbitol in methanol or ethanol at 275° C. and 4000 psi (27.6 MPa), for one hour using 0.8 weight percent of nickel on silica/alumina and 20.5 mol percent of the indicated corresponding alkoxide base.

|     | MeOH NaOCH$_3$ | EtOH NaOEt |
|-----|----------------|------------|
| EG  | 25             | 24         |
| PG  | 27             | 39         |
| G   | 8              | 4          |
| T   | 2              | 3          |
| X   | 3              | 0          |
| Alc | 2              | 7          |
| Oth | 25             | 23         |
| Unr | 8              | 0          |

TABLE 3

Weight percent of products from hydrogenolysis of xylitol in methanol at 275° C. and 4000 psi (27.6 MPa), for one hour using 0.8 weight percent of nickel on silica/alumina and 20.5 mol percent of the indicated base.

|     | NaOMe* | Ca(OH)$_2$ | NaOH | Zn(OH)$_2$** | Al(OH)$_3$** |
|-----|--------|------------|------|--------------|--------------|
| EG  | 45     | 41         | 46   | 28           | 29           |

TABLE 3-continued

Weight percent of products from hydrogenolysis of xylitol in methanol at 275° C. and 4000 psi (27.6 MPa), for one hour using 0.8 weight percent of nickel on silica/alumina and 20.5 mol percent of the indicated base.

|     | NaOMe* | Ca(OH)$_2$ | NaOH | Zn(OH)$_2$** | Al(OH)$_3$** |
|-----|--------|------------|------|--------------|--------------|
| PG  | 33     | 34         | 35   | 19           | 16           |
| G   | 5      | 4          | 4    | 17           | 23           |
| T   | 2      | 2          | 1    | 4            | 2            |
| Alc | 1      | 2          | 1    | 1            | 1            |
| Oth | 14     | 16         | 12   | 25           | 13           |
| Unr | 0      | 1          | 1    | 6            | 16           |

TABLE 4

Weight percent of products from hydrogenolysis of xylitol in various alcohols at 275° C. and 4000 psi (27.6 MPa) for one hour using 0.8 weight percent of nickel on silica/alumina and 20.5 mol percent of the indicated base.

|     | i-PrOH i-PrOAl | t-BuOH t-BuOK | sec-BuOH sec-BuOAl |
|-----|----------------|---------------|--------------------|
| EG  | 15             | 32            | 22                 |
| PG  | 22             | 34            | 28                 |
| G   | 4              | 2             | 3                  |
| T   | 1              | 2             | 0                  |
| Alc | 11             | 8             | 10                 |
| Oth | 47             | 22            | 37                 |
| Unr | 0              | 0             | 0                  |

TABLE 5

Weight percent of products from hydrogenolysis of xylitol in various nonprotic solvents at 275° C. and 4000 psi (27.6 MPa) for one hour using 0.8 weight percent of nickel on silica/alumina and 20.5 mol percent of the indicated base.

|     | THF NaOMe | THF NaOEt | Cyclohexane NaOMe |
|-----|-----------|-----------|-------------------|
| EG  | 22        | 16        | 24                |
| PG  | 47        | 39        | 36                |
| G   | 2         | 2         | 1                 |
| T   | 1         | 5         | 1                 |
| Alc | 7         | 12        | 2                 |
| Oth | 20        | 23        | 35                |
| Unr | 1         | 3         | 1                 |

TABLE 6

Weight percent of products from hydrogenolysis of xylitol in methanol or ethanol at 275° C. and 2000 or 4000 psi (13.8 or 27.6 MPa) for one hour using 0.8 weight percent of nickel on silica/alumina and 20.5 mol percent of calcium hydroxide.

|     | MeOH 2000 psi | MeOH* 4000 psi | EtOH 2000 psi | EtOH 4000 psi |
|-----|---------------|----------------|---------------|---------------|
| EG  | 30            | 41             | 21            | 34            |
| PG  | 31            | 34             | 22            | 35            |
| G   | 4             | 4              | 9             | 6             |
| T   | 4             | 2              | 4             | 2             |
| Alc | 2             | 2              | 3             | 5             |
| Oth | 27            | 16             | 34            | 18            |
| Unr | 2             | 1              | 7             | 0             |

*repeated from Table 3

TABLE 7

Weight percent of products from hydrogenolysis of xylitol in methanol at various temperatures and 4000 psi (27.6 MPa) for one hour using 0.8 weight percent of nickel on silica/alumina and 20.5 mol percent of sodium methoxide.

|     | 215° | 240° | 275°* | 310° |
|-----|------|------|-------|------|
| EG  | 20   | 46   | 45    | 33   |
| PG  | 14   | 30   | 33    | 24   |

TABLE 7-continued

Weight percent of products from hydrogenolysis of xylitol in methanol at various temperatures and 4000 psi (27.6 MPa) for one hour using 0.8 weight percent of nickel on silica/alumina and 20.5 mol percent of sodium methoxide.

|     | 215° | 240° | 275°* | 310° |
|-----|------|------|-------|------|
| G   | 5    | 14   | 5     | 5    |
| T   | 1    | 1    | 2     | 3    |
| Alc | 0    | 1    | 1     | 3    |
| Oth | 9    | 7    | 14    | 30   |
| Unr | 51   | 1    | 0     | 2    |

*repeated from Table 1

TABLE 8

Weight percent of products from hydrogenolysis of xylitol in methanol or ethanol at 275° C. and 2000 or 4000 psi (13.8 or 27.6 MPa) for one hour using 0.8 weight percent of nickel on silica/alumina or 0.6 weight percent of palladium on carbon and various amounts of calcium hydroxide or sodium methoxide.

|     | MeOH 4000 psi Nickel NaOMe: 10 mol % | EtOH** 2000 psi Nickel Ca(OH)$_2$: 20 mol % | EtOH* 2000 psi Palladium Ca(OH)$_2$: 12 mol % |
|-----|------|------|------|
| EG  | 34   | 21   | 26   |
| PG  | 22   | 22   | 31   |
| G   | 11   | 9    | 4    |
| T   | 3    | 4    | 1    |
| Alc | 1    | 3    | 3    |
| Oth | 17   | 34   | 28   |
| Unr | 12   | 7    | 7    |

*20% xylitol
**repeated from Table 6

TABLE 9

Weight percent of products from hydrogenolysis of sorbitol in methanol or ethanol at 275° C. and 4000 psi (27.6 MPa) for one hour using 0.8 weight percent of nickel on silica/alumina and various amounts of the corresponding sodium alkoxide base.

|     | Methanol | | Ethanol | | |
|-----|------|------|------|------|------|
|     | 20.5 mol % | 40 mol % | 10 mol % | 20.5 mol % | 40 mol % |
| EG  | 25 | 35 | 22 | 23 | 20 |
| PG  | 26 | 40 | 26 | 31 | 42 |
| G   | 13 | 4  | 11 | 6  | 4  |
| T   | 3  | 3  | 3  | 2  | 2  |
| X   | 1  | 3  | 3  | 3  | 2  |
| Alc | 1  | 2  | 5  | 6  | 6  |
| Oth | 31 | 13 | 30 | 29 | 24 |
| Unr | 0  | 0  | 0  | 0  | 0  |

TABLE 10

Weight percent of products from hydrogenolysis of xylitol in methanol or ethanol at 275° C. and 4000 psi (27.6 MPa) for one hour using 0.8 weight percent of nickel on silica/alumina and various amounts of the corresponding sodium alkoxide base.

|     | Methanol | | | | Ethanol | |
|-----|------|------|------|------|------|------|
|     | 1 mol % | 5 mol % | 10 mol % | 20.5 mol %* | 10 mol % | 20.5 mol % |
| EG  | 20 | 25 | 34 | 45 | 36 | 34 |
| PG  | 17 | 19 | 22 | 33 | 22 | 34 |
| G   | 4  | 6  | 11 | 5  | 16 | 3  |
| T   | 1  | 2  | 3  | 2  | 1  | 1  |
| Alc | 0  | 1  | 1  | 1  | 4  | 7  |
| Oth | 24 | 22 | 17 | 14 | 16 | 21 |
| Unr | 34 | 25 | 12 | 0  | 5  | 0  |

*repeated from Table 1

TABLE 11

Weight percent of products from hydrogenolysis of erythritol or glycerol in methanol or ethanol at 275° C. and 4000 psi (27.6 MPa) for one hour using 0.8 weight percent of nickel on silica/alumina and 20 mol percent of the corresponding sodium alkoxide base.

|     | Glycerol MeOH | Glycerol EtOH | Erythritol MeOH |
|-----|------|------|------|
| EG  | 15   | 9    | 45   |
| PG  | 70   | 65   | 22   |
| G   | 2    | 2    | 2    |
| E   | 0    | 1    | 1    |
| Alc | 2    | 4    | 3    |
| Oth | 11   | 19   | 27   |

BEST MODE

The best mode for carrying out the process of the invention is illustrated by the procedure described for the Examples, above, and, in particular, in the hydrogenolysis of xylitol in methanol using a strong base.

INDUSTRIAL APPLICABILITY

The process of the invention has obvious industrial applicability as a method for producing ethylene glycol and other useful products from renewable biomass resources.

While the preferred embodiments of the invention are described by the above, it is to be understood that the invention is not limited to the precise embodiments herein disclosed and that the right is reserved to all changes and modifications coming within the scope of the invention as defined in the following claims:

I claim:

1. Process for hydrogenolysis of polyols to a reaction product mixture consisting essentially of a major fraction of ethylene glycol and propylene glycol and a minor fraction of glycerol, other products and unreacted starting material, in which process the polyols are contacted and reacted with hydrogen in the presence of a substantially nonaqueous solvent, a hydrogenation catalyst and at least 10 mol percent of a base at a temperature of at least 225° C., said base selected from the oxide, hydroxide or alkoxide of an alkali metal, calcium, strontium or barium.

2. Process of claim 1 wherein the amount of base is at least 15 mol percent.

3. Process of claim 1 wherein the solvent is selected from methanol, ethanol, propanols, butanols, ethylene glycol, propylene glycol, glycerol, tetrahydrofuran and cyclohexane.

4. Process of claim 1 wherein the solvent is a $C_{1-4}$ monohydric alcohol.

5. Process of claim 4 wherein the catalyst is nickel.

6. Process of claim 5 wherein the base is the alkoxide, hydroxide or oxide of calcium or sodium and the solvent is methanol or ethanol.

7. Process of claim 6 wherein the base is the alkoxide.

8. Process of claim 7 wherein the temperature is 235° to 325° C. and the amount of base is at least 20 mol percent.

9. Process of claim 8 wherein the solvent is methanol, the polyols are pentitols, hexitols or a mixture thereof and the base is sodium methoxide.

10. Process for hydrogenolysis of xylitol to a reaction product mixture consisting essentially of a major fraction of ethylene glycol and propylene glycol and a minor fraction of glycerol, other products and unreacted starting material, in which process the xylitol is contacted and reacted with hydrogen in the presence of substantially nonaqueous methanol or ethanol, a nickel hydrogenation catalyst and at least 10 mol percent of a base at 235° to 325° C., said base selected from the oxide, hydroxide or alkoxide of an alkali metal, calcium, strontium or barium.

11. Process of claim 10 wherein the amount of base is at least 20 mol percent.

12. Process of claim 11 wherein the xylitol is contacted and reacted with hydrogen in methanol and the base is the alkoxide, hydroxide or oxide of sodium or calcium.

13. Process for hydrogenolysis of sorbitol to a reaction product mixture consisting essentially of a major fraction of ethylene glycol and propylene glycol and a minor fraction of glycerol, other products and unreacted starting material, in which process the sorbitol is contacted and reacted with hydrogen in the presence of substantially nonaqueous methanol or ethanol, a nickel hydrogenation catalyst and at least 20 mol percent of a base at 235° to 325° C., said base selected from the oxide, hydroxide or alkoxide of an alkali metal, calcium, strontium or barium.

14. Process of claim 13 wherein the amount of base is at least 25 mol percent.

15. Process of claim 13 wherein the amount of base is at least 40 mol percent.

16. Process of claim 14 wherein the sorbitol is contacted and reacted with hydrogen in methanol and the base is the alkoxide, hydroxide or oxide of sodium or calcium.

* * * * *